United States Patent
Arnin

(10) Patent No.: US 11,723,691 B2
(45) Date of Patent: Aug. 15, 2023

(54) BIASING DEVICE FOR SPINAL DEVICE

(71) Applicant: Apifix Ltd., Carmiel (IL)

(72) Inventor: Uri Arnin, Kiryat Tivon (IL)

(73) Assignee: ApiFix LTD

( * ) Notice: Subject to any disclaimer, the term of this patent is extended or adjusted under 35 U.S.C. 154(b) by 657 days.

(21) Appl. No.: 16/726,872

(22) Filed: Dec. 25, 2019

(65) Prior Publication Data
US 2021/0196327 A1 Jul. 1, 2021

(51) Int. Cl.
*A61B 17/70* (2006.01)
*A61B 17/56* (2006.01)
*A61B 17/68* (2006.01)
*A61B 17/00* (2006.01)

(52) U.S. Cl.
CPC ............ *A61B 17/7014* (2013.01); *A61B 2017/00407* (2013.01); *A61B 2017/564* (2013.01); *A61B 2017/681* (2013.01)

(58) Field of Classification Search
CPC ............ A61B 17/7013; A61B 17/7014; A61B 17/7019; A61B 17/702–7031; A61B 17/7025; A61B 17/8004; A61B 17/8009; A61B 17/8023
See application file for complete search history.

(56) References Cited

U.S. PATENT DOCUMENTS

| | | | | |
|---|---|---|---|---|
| 4,157,715 A * | 6/1979 | Westerhoff | ......... | A61B 17/8004 606/58 |
| 6,241,730 B1 * | 6/2001 | Alby | ................. | A61B 17/7023 403/120 |
| 6,402,750 B1 * | 6/2002 | Atkinson | ............... | A61B 17/70 606/279 |
| 7,029,475 B2 * | 4/2006 | Panjabi | .............. | A61B 17/7007 606/279 |
| 7,207,992 B2 * | 4/2007 | Ritland | .............. | A61B 17/7007 606/86 A |
| 7,335,200 B2 * | 2/2008 | Carli | ................... | A61B 17/7059 606/246 |
| 7,361,196 B2 * | 4/2008 | Fallin | ................. | A61B 17/7052 623/61 |
| 7,621,912 B2 * | 11/2009 | Harms | ............... | A61B 17/7004 606/279 |

(Continued)

FOREIGN PATENT DOCUMENTS

WO 2008082085 7/2008

OTHER PUBLICATIONS

PCT/IL20/51308, International Search Report and Written Opinion, 13 pgs, dated May 19, 2021.

(Continued)

*Primary Examiner* — Lynnsy M Summitt
(74) *Attorney, Agent, or Firm* — Gerald W. Roberts; John V. Daniluck; Dentons Bingham Greenebaum LLP

(57) ABSTRACT

A spinal device includes a rod which has a first end disposed in a housing and a second end which protrudes out of the housing through an aperture and which is movable to protrude more out of the housing or less out of the housing. A biasing device, mounted on the rod, includes a series of connected at-least partial coils. A first end of the biasing device is arranged to abut against the housing and a second end of the biasing device, opposite to the first end, is affixed to the rod.

15 Claims, 1 Drawing Sheet

(56) References Cited

U.S. PATENT DOCUMENTS

| | | | | |
|---|---|---|---|---|
| 7,621,940 B2* | 11/2009 | Harms | A61B 17/7026 | 606/257 |
| 7,635,364 B2* | 12/2009 | Barrall | A61B 17/8023 | 606/70 |
| 7,641,675 B2* | 1/2010 | Lindemann | A61B 17/8085 | 606/283 |
| 7,655,041 B2* | 2/2010 | Clifford | A61F 2/3836 | 623/13.12 |
| 7,722,649 B2* | 5/2010 | Biedermann | A61B 17/7032 | 606/257 |
| 7,763,056 B2* | 7/2010 | Dalton | A61B 17/7059 | 606/280 |
| 7,766,915 B2* | 8/2010 | Jackson | A61B 17/7037 | 606/86 A |
| 7,811,309 B2* | 10/2010 | Timm | A61B 17/7025 | 606/255 |
| 7,828,823 B2* | 11/2010 | Rogeau | A61B 17/7025 | 403/120 |
| 7,854,752 B2* | 12/2010 | Colleran | A61B 17/7062 | 606/279 |
| 7,896,904 B2* | 3/2011 | Perez-Cruet | A61B 17/7005 | 606/257 |
| 7,935,134 B2* | 5/2011 | Reglos | A61B 17/7037 | 606/259 |
| 8,075,595 B2* | 12/2011 | Kim | A61B 17/70 | 606/279 |
| 8,088,166 B2* | 1/2012 | Makower | A61F 2/0811 | 623/20.14 |
| 8,172,880 B2* | 5/2012 | Graf | A61B 17/7025 | 606/257 |
| 8,202,301 B2* | 6/2012 | Prevost | A61B 17/702 | 606/279 |
| 8,241,362 B2* | 8/2012 | Voorhies | A61B 17/7071 | 623/17.16 |
| 8,292,927 B2* | 10/2012 | Rouleau | A61B 17/7025 | 606/255 |
| 8,328,962 B2* | 12/2012 | Schussler | F16F 1/021 | 623/17.13 |
| 8,353,936 B2* | 1/2013 | Biedermann | A61B 17/7028 | 606/279 |
| 8,361,118 B2* | 1/2013 | Biedermann | A61B 17/702 | 606/259 |
| 8,372,116 B2* | 2/2013 | Foley | A61B 17/7031 | 606/247 |
| 8,449,576 B2* | 5/2013 | Lechmann | A61B 17/7023 | 606/259 |
| 8,486,112 B2* | 7/2013 | Fanger | A61B 17/7005 | 606/267 |
| 8,491,637 B2* | 7/2013 | Matthis | A61B 17/702 | 606/264 |
| 8,506,604 B2* | 8/2013 | Timm | A61B 17/7007 | 606/279 |
| 8,518,084 B2* | 8/2013 | Biedermann | A61B 17/7025 | 606/259 |
| 8,668,720 B2* | 3/2014 | Perez-Cruet | A61B 17/7028 | 606/255 |
| 8,740,944 B2* | 6/2014 | Trieu | A61B 17/7011 | 606/254 |
| 8,777,995 B2* | 7/2014 | McClintock | A61B 17/7014 | 606/260 |
| 8,795,336 B2* | 8/2014 | Biedermann | A61B 17/702 | 606/267 |
| 8,801,795 B2* | 8/2014 | Makower | A61B 17/68 | 623/20.14 |
| 8,808,328 B2* | 8/2014 | Hwang | A61B 17/7049 | 606/57 |
| 8,808,379 B2* | 8/2014 | Abdou | A61B 17/702 | 623/17.11 |
| 8,858,600 B2* | 10/2014 | Brown | A61B 17/7025 | 606/252 |
| 8,876,867 B2* | 11/2014 | Hestad | A61B 17/7032 | 606/265 |
| 8,894,688 B2* | 11/2014 | Suh | A61B 17/7014 | 606/259 |
| 8,920,473 B2* | 12/2014 | Trautwein | A61B 17/7025 | 606/259 |
| 8,974,497 B2* | 3/2015 | Cho | A61B 17/7034 | 606/255 |
| 8,974,504 B2* | 3/2015 | Hess | A61B 17/8028 | 606/282 |
| 9,072,544 B2* | 7/2015 | Fortin | A61B 17/7023 | |
| 9,089,369 B2* | 7/2015 | Biedermann | A61B 17/7026 | |
| 9,107,702 B2* | 8/2015 | Casutt | A61B 17/70 | |
| 9,138,263 B2* | 9/2015 | Krause | A61F 2/44 | |
| 9,333,009 B2* | 5/2016 | Kroll | A61B 17/7053 | |
| 9,510,871 B2* | 12/2016 | Ledet | A61B 17/7059 | |
| 10,159,475 B2* | 12/2018 | Frey | A61B 17/70 | |
| 10,245,081 B2 | 4/2019 | Arnin | | |
| 10,335,199 B2* | 7/2019 | Simpson | A61B 17/7014 | |
| 10,441,320 B2* | 10/2019 | Lai | A61B 17/705 | |
| 10,595,902 B2* | 3/2020 | Ingalhalikar | A61B 17/7004 | |
| 10,610,262 B2* | 4/2020 | Castelein | A61B 17/7049 | |
| 10,835,384 B2* | 11/2020 | Bydon | A61B 17/7031 | |
| 10,842,535 B2* | 11/2020 | Krause | A61B 17/7029 | |
| 11,039,859 B2* | 6/2021 | Simpson | A61B 17/7017 | |
| 2003/0204190 A1* | 10/2003 | Li | A61B 17/663 | 606/90 |
| 2005/0113927 A1* | 5/2005 | Malek | A61B 17/7049 | 606/247 |
| 2005/0171543 A1* | 8/2005 | Timm | A61B 17/7034 | 606/279 |
| 2005/0177164 A1* | 8/2005 | Walters | A61B 17/8685 | 606/279 |
| 2005/0182409 A1* | 8/2005 | Callahan | A61B 17/704 | 606/328 |
| 2005/0246034 A1* | 11/2005 | Soubeiran | A61B 17/7216 | 623/23.45 |
| 2005/0261682 A1* | 11/2005 | Ferree | A61B 17/7025 | 606/247 |
| 2006/0009767 A1* | 1/2006 | Kiester | A61B 17/70 | 606/279 |
| 2006/0155279 A1* | 7/2006 | Ogilvie | A61B 17/7031 | 606/328 |
| 2006/0189985 A1* | 8/2006 | Lewis | A61B 17/7026 | 606/259 |
| 2006/0247637 A1* | 11/2006 | Colleran | A61B 17/7014 | 606/279 |
| 2007/0088359 A1* | 4/2007 | Woods | A61B 17/7049 | 606/86 A |
| 2007/0270838 A1* | 11/2007 | Bruneau | A61B 17/7025 | 606/250 |
| 2008/0065073 A1* | 3/2008 | Perriello | A61B 17/7025 | 606/100 |
| 2008/0147125 A1* | 6/2008 | Colleran | A61B 17/8004 | 606/280 |
| 2008/0154312 A1* | 6/2008 | Colleran | A61B 17/8004 | 606/283 |
| 2008/0161931 A1 | 7/2008 | Perez-Cruet et al. | | |
| 2008/0177319 A1* | 7/2008 | Schwab | A61B 17/7014 | 606/257 |
| 2008/0262554 A1* | 10/2008 | Hayes | A61B 17/7023 | 606/257 |
| 2009/0030465 A1* | 1/2009 | Altarac | A61B 17/7023 | 606/264 |
| 2009/0099608 A1* | 4/2009 | Szczesny | A61B 17/7028 | 606/257 |
| 2009/0105760 A1* | 4/2009 | Frey | A61B 17/7023 | 606/300 |
| 2009/0156999 A1 | 6/2009 | Adams et al. | | |
| 2009/0228045 A1* | 9/2009 | Hayes | A61B 17/7023 | 606/264 |
| 2009/0234388 A1* | 9/2009 | Patterson | A61B 17/702 | 606/246 |
| 2009/0306717 A1* | 12/2009 | Kercher | A61B 17/7011 | 606/279 |
| 2010/0036423 A1* | 2/2010 | Hayes | A61B 17/7025 | 606/260 |

(56) References Cited

U.S. PATENT DOCUMENTS

| | | | | |
|---|---|---|---|---|
| 2010/0063547 A1* | 3/2010 | Morin | A61B 17/7023 | 606/278 |
| 2010/0131010 A1* | 5/2010 | Graf | A61B 17/7007 | 606/264 |
| 2010/0145386 A1* | 6/2010 | Greenhalgh | A61B 17/8863 | 606/279 |
| 2011/0009906 A1* | 1/2011 | Hestad | A61B 17/7022 | 606/264 |
| 2011/0152941 A1* | 6/2011 | Graf | A61B 17/7046 | 606/279 |
| 2011/0166601 A1* | 7/2011 | Cain | A61B 17/7022 | 606/279 |
| 2011/0264144 A1* | 10/2011 | Arthur | A61B 17/8004 | 606/246 |
| 2013/0282064 A1* | 10/2013 | Arnin | A61B 17/8009 | 606/258 |
| 2013/0296857 A1* | 11/2013 | Barnett | A61B 17/66 | 606/57 |
| 2013/0338712 A1* | 12/2013 | Massenzio | A61B 17/7028 | 606/252 |
| 2013/0338713 A1* | 12/2013 | Kawakami | A61B 17/7014 | 606/258 |
| 2014/0200615 A1* | 7/2014 | Yeh | A61B 17/7028 | 606/255 |
| 2014/0276822 A1* | 9/2014 | Cresina | A61B 17/6416 | 606/57 |
| 2015/0190175 A1* | 7/2015 | Oldakowski | A61B 17/7007 | 606/246 |
| 2016/0030088 A1* | 2/2016 | Lim | A61B 17/8009 | 606/257 |
| 2020/0214743 A1* | 7/2020 | Eckhof | A61B 17/7026 | |

OTHER PUBLICATIONS

PCT/IL20/51308, International Preliminary Report on Patentability, 12 pgs, dated Dec. 7, 2021.

* cited by examiner

BIASING DEVICE FOR SPINAL DEVICE

FIELD OF THE INVENTION

The present invention relates generally to spinal implants and prostheses, and particularly to an add-on or integral biasing device for a spinal device, such as a spinal rod.

BACKGROUND OF THE INVENTION

Scoliosis is a spinal deformity affecting many people. Current surgical treatment involves affixing long fusion rods to the spine by pedicle screws. The rod system is intended to force the deformed spine into a more healthy position.

Unfortunately, there are severe shortcomings to this procedure; the deformation is rarely perfectly corrected, the long fusion for life is not a desired clinical situation and failures are not uncommon.

U.S. patent Ser. No. 10/245,081 to Arnin describes an improved ratcheted spinal device that includes a rod that can move out of a housing. The amount the rod protrudes out of the housing can be lengthened or shortened using a ratchet mechanism. The rod can be connected to standard pedicle screws as well as to other spinal rods or spinal structure, using appropriate connectors.

SUMMARY OF THE INVENTION

The present invention seeks to provide an improved spinal device or accessory for a spinal device, namely an add-on or integral biasing device for a spinal device, as is described more in detail hereinbelow.

There is thus provided in accordance with a non-limiting embodiment of the present invention a spinal device including a rod which has a first end disposed in a housing and a second end which protrudes out of the housing through an aperture and which is movable to protrude more out of the housing or less out of the housing, and a biasing device, mounted on the rod, which includes a series of connected at-least partial coils, wherein a first end of the biasing device is arranged to abut against the housing and a second end of the biasing device, opposite to the first end, is affixed to the rod.

The at-least partial coils may include full coils, or instead, a series of connected partial coils that do not extend completely around the rod but instead subtend an angle of less than 360° and each pair of neighboring coils of the partial coils are connected by a connection member and the connection members are separated from one another by a circumferential gap.

In accordance with an embodiment of the present invention a first end of the biasing device is arranged to abut against the housing and a second end of the biasing device, opposite to the first end, is provided with a fastener to affix the second end to the rod.

In accordance with an embodiment of the present invention axial fixation of the second end determines a pretension of the biasing device.

In accordance with an embodiment of the present invention the rod is coupled with a ratchet mechanism for controlling an amount the rod protrudes out of the housing.

In accordance with an embodiment of the present invention a first polyaxial-joint attachment member is at the second end of the rod and a second polyaxial-joint attachment member is at a portion of the housing.

In accordance with an embodiment of the present invention a method for adjusting curvature of a spine includes mounting a biasing device on a rod of a spinal device which is installed on spinal structure, the biasing device including a series of connected partial coils that do not extend completely around the rod but instead subtend an angle of less than 360° and each pair of neighboring coils of the partial coils are connected by a connection member and the connection members are separated from one another by a circumferential gap, and using the biasing device to apply an urging force to the rod and to the spinal structure.

BRIEF DESCRIPTION OF DRAWINGS

The present invention will be understood and appreciated more fully from the following detailed description, taken in conjunction with the drawings in which.

DETAILED DESCRIPTION OF EMBODIMENTS

Figure 1:
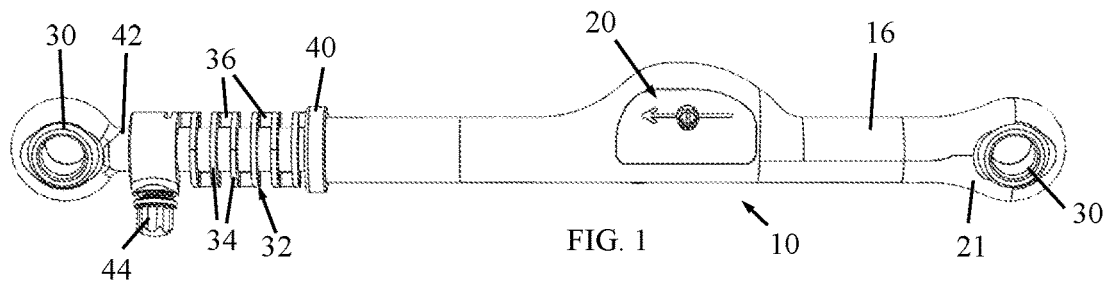
FIG. 1 is a simplified pictorial illustration of a spinal device, constructed and operative in accordance with an embodiment of the invention.
Figure 2:
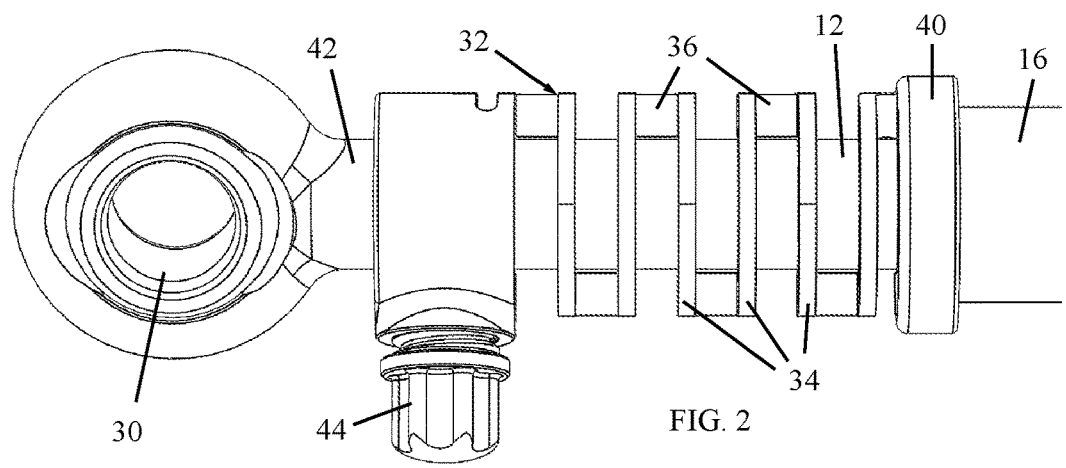
FIG. 2 is a simplified enlarged illustration of a biasing device of the spinal device of FIG. 1.
Figure 3:
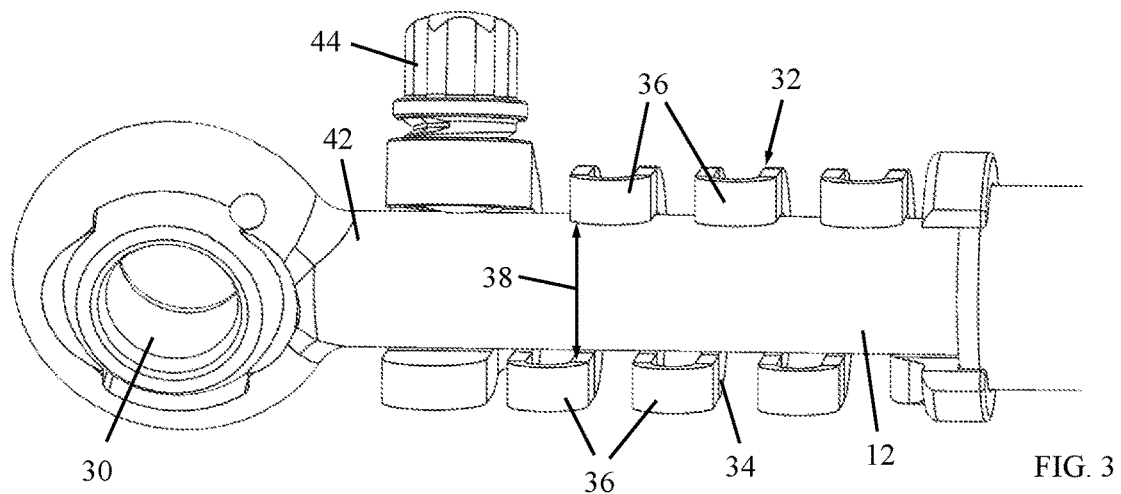
FIG. 3 is another simplified illustration of the biasing device, showing circumferential gaps between ends of partial coils of the biasing device.

Reference is now made to FIGS. 1-3, which illustrate a spinal device 10, constructed and operative in accordance with a non-limiting embodiment of the invention.

Spinal device 10 includes a rod 12 which has a first end 14 (FIG. 4) disposed in a housing 16 and a second end 18 which protrudes out of housing 16 through an aperture 19 and which is movable to protrude more out of housing 16 or less out of housing 16. The term "rod" throughout encompasses any element with a round or non-round, regular or irregular perimeter, such as but not limited to, a rod, bar, lug, wire, post and others.

Figure 4:
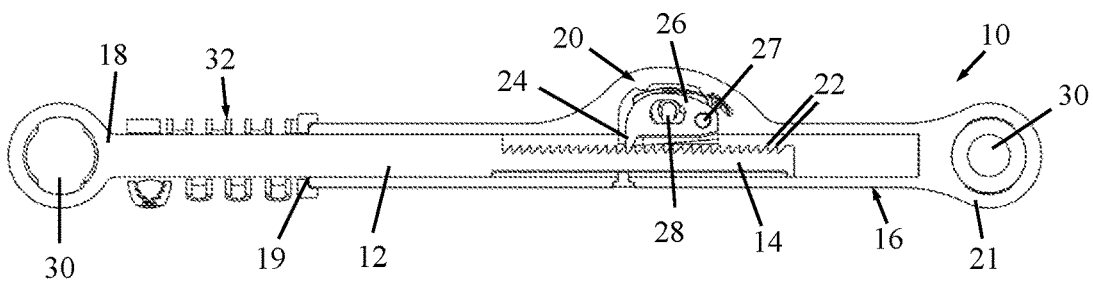
FIG. 4 is a simplified sectional illustration of the spinal device.

As seen in FIG. 4, rod 12 may be coupled with a ratchet mechanism 20 for controlling the amount rod 12 protrudes out of housing 16. Ratchet mechanism 20 may include ratchet teeth 22 formed along an axial portion of rod 12, and a pawl 24 arranged to catch on one of the teeth 22. Pawl 24 may extend from a controller element 26 mounted about a pivot 27 and provided with an eccentric cam 28. Rotation of eccentric cam 28 moves pawl 24 to one of three positions: a) in ratchet engagement with teeth 22 so that rod 12 can incrementally move in one direction, b) in locked engagement with teeth 22 so that rod 12 cannot move at all, and c) moved out of engagement with teeth 22 so that rod 12 can move in both directions freely. Other ratchet mechanisms can be used. Alternatively, no ratchet mechanism is used; for example, rod 12 may be urged by an internal spring inside housing 16.

Two polyaxial-joint attachment members 30 (such as but not limited to, a bearing race or simple hole) may be provided in device 10, one at the second end 18 of rod 12 and the other one at another portion 21 of housing 16. Both polyaxial-joint attachment members 30 are used to attach device 10 to available bone structure of the spine, such as by means of pedicle screws that pass through members 30. It is noted that even after tightening a fastener to member 30, the fastener securely holds the pedicle screw in place while enabling polyaxial rotation, as shown in U.S. patent Ser. No. 10/245,081.

Device 10 includes a biasing device 32, which may be an add-on accessory which can be added to device 10 prior to or after installation in a patient; alternatively device 10 can be provided by the manufacturer with biasing device 32.

The biasing device 32 may include a series of connected at-least partial coils 34 (e.g., spring coils). In one embodiment, coils 34 are full coils (full 360°). In another embodiment, coils 34 are partial coils that do not extend completely around rod 12 but instead subtend an angle of less than 360° and each pair of neighboring partial coils are connected by a connection member 36. As seen in FIG. 3, the connection members 36 are separated from one another by a circumferential gap 38.

If biasing device 32 includes partial coils 34, it can be placed directly over any axial portion of rod 12 as opposed to full coils which have to be slipped over an end of rod 12 and then slid axially to a desired axial position (a device with full coils can be supplied by the manufacturer. This feature allows adding biasing device 32 to device 10 even after device 10 has been installed in a patient.

A first end 40 of biasing device 32 is arranged to abut against housing 16 and a second end 42, opposite to the first end 40, is provided with a fastener 44, such as a set screw to affix the second end 42 to rod 12. The axial fixation of the second end 42 determines the pretension of biasing device 32.

After installation of device 10 in a patient, in a typical treatment plan, the biasing device 32 provides an urging force to the opposite ends of device 10, such as to help straighten the patient's spine.

What is claimed is:

1. A spinal device comprising:
   a rod which has a first end disposed in a housing and a second end which protrudes out of said housing through an aperture and which is movable to protrude more out of said housing or less out of said housing; and
   a biasing device, mounted on said rod, which comprises a series of connected at-least partial coils,
   wherein a first end of said biasing device is arranged to abut against said housing,
   wherein a second end of said biasing device, opposite to said first end, is affixed to said rod, and
   wherein said at-least partial coils do not extend completely around said rod but instead subtend an angle of less than 360° and each pair of neighboring coils of said at-least partial coils are connected by a connection member and said connection members are separated from one another by a circumferential gap.

2. The spinal device according to claim 1, wherein axial fixation of said second end determines a pretension of said biasing device.

3. The spinal device according to claim 1, wherein said rod is coupled with a ratchet mechanism for controlling an amount said rod protrudes out of said housing.

4. The spinal device according to claim 1, wherein a first polyaxial-joint attachment member is at said second end of said rod and a second polyaxial-joint attachment member is at a portion of said housing.

5. A method for adjusting curvature of a spine, the method comprising:
   mounting a biasing device directly over an axial portion of a rod of a spinal device which is installed on a spinal structure without axially slipping said biasing device over any end of said rod, wherein said biasing device comprises a series of connected at-least partial coils;
   abutting a first end of said biasing device against a housing; and
   affixing a second end of said biasing device, opposite to said first end of said biasing device, to said rod,
   wherein said biasing device applies an urging force to said rod and to said spinal structure.

6. The method of claim 5, wherein affixing said second end of said biasing device to said rod comprises determining a pretension of said biasing device.

7. The method of claim 5, comprising:
   adjusting a position of said rod relative to said housing.

8. The method of claim 7, wherein adjusting said position of said rod relative to said housing comprises ratcheting said position of said rod relative to said housing.

9. A spinal device comprising:
   an implantable housing;
   an implantable elongated member including a first member end disposed in said implantable housing, said implantable elongated member including a second member end protruding from said implantable housing; and
   an implantable biasing device including a first device end abutting said implantable housing, said implantable biasing device including a second device end coupled to said implantable elongated member, said implantable biasing device including a series of connected partial coils extending partially and not completely around said implantable elongated member.

10. The spinal device according to claim 9, wherein said series of connected partial coils subtends an angle of less than 360°.

11. The spinal device according to claim 10, wherein said series of connected partial coils includes pairs of connected neighboring coils, and wherein said pairs of connected neighboring coils are circumferentially separated from one another by a circumferential gap.

12. The spinal device according to claim 11, wherein said implantable elongated member is at least one of at least partially extendable from said housing and at least partially retractable into said housing.

13. The spinal device according to claim 12, comprising:
   a ratchet mechanism coupled to said implantable elongated member,
   wherein said ratchet mechanism is operable to cause at least one of an extension of said implantable elongated member from said housing and a retraction of said implantable elongated member into said housing.

14. The spinal device according to claim 13, comprising:
   a first polyaxial-joint attachment member at said second member end; and
   a second polyaxial-joint attachment member at a portion of said housing.

15. The spinal device according to claim 11, comprising:
   a first polyaxial-joint attachment member at said second member end; and
   a second polyaxial-joint attachment member at a portion of said housing.

* * * * *